United States Patent
Mestha et al.

(10) Patent No.: US 9,301,710 B2
(45) Date of Patent: *Apr. 5, 2016

(54) PROCESSING A VIDEO FOR RESPIRATION RATE ESTIMATION

(75) Inventors: Lalit Keshav Mestha, Fairport, NY (US); Edgar A. Bernal, Webster, NY (US); Beilei Xu, Penfield, NY (US)

(73) Assignee: Xerox Corporation, Norwalk, CT (US)

(*) Notice: Subject to any disclaimer, the term of this patent is extended or adjusted under 35 U.S.C. 154(b) by 959 days.

This patent is subject to a terminal disclaimer.

(21) Appl. No.: 13/529,648

(22) Filed: Jun. 21, 2012

(65) Prior Publication Data

US 2013/0324875 A1 Dec. 5, 2013

Related U.S. Application Data

(63) Continuation-in-part of application No. 13/486,637, filed on Jun. 1, 2012.

(51) Int. Cl.
- *A61B 5/05* (2006.01)
- *A61B 5/107* (2006.01)
- *A61B 5/00* (2006.01)
(Continued)

(52) U.S. Cl.
CPC ............ *A61B 5/1077* (2013.01); *A61B 5/0064* (2013.01); *A61B 5/0816* (2013.01); *A61B 5/1128* (2013.01); *A61B 5/1135* (2013.01); *G01B 11/2527* (2013.01); *G06T 7/0057* (2013.01); *G06T 7/206* (2013.01); *G06K 9/0053* (2013.01); *G06T 2207/10016* (2013.01); *G06T 2207/10024* (2013.01); *G06T 2207/10048* (2013.01); *G06T 2207/10152* (2013.01); *G06T 2207/20044* (2013.01);
(Continued)

(58) Field of Classification Search
USPC .......................................................... 600/411
See application file for complete search history.

(56) References Cited

U.S. PATENT DOCUMENTS

| 5,107,845 A | 4/1992 | Guern et al. |
| 5,800,360 A | 9/1998 | Kisner et al. |

(Continued)

OTHER PUBLICATIONS

Johansson et al (heart rate variability estimation and data visualization for use in stress level determination in neuro-intensive care patients).*

(Continued)

*Primary Examiner* — Joel F Brutus
(74) *Attorney, Agent, or Firm* — Philip E. Blair; Fleit Gibbons Gutman Bongini & Bianco P.L.

(57) ABSTRACT

What is disclosed is a system and method for estimating a respiration rate by analyzing distortions in reflections of structured illumination patterns captured in a video containing a view of a subject's thoracic region. In one embodiment, a video of a target region of a body of a subject of interest is received. Video image frames are processed to estimate 3D time-series data for the target region. As more fully disclosed herein, the subject's respiration rate is estimated from the 3D time-series data. Measurements can be acquired under a diverse set of lighting conditions. The teachings hereof provide a non-contact approach to patient respiratory function monitoring that is useful for intensive care units and for monitoring at homes, and which aid in the detection of sudden deterioration of physiological conditions due to changes in respiration rates. The teachings hereof provide an effective tool for non-contact respiratory function study and analysis.

20 Claims, 11 Drawing Sheets

(51) Int. Cl.
| | |
|---|---|
| *A61B 5/08* | (2006.01) |
| *A61B 5/11* | (2006.01) |
| *A61B 5/113* | (2006.01) |
| *G01B 11/25* | (2006.01) |
| *G06T 7/00* | (2006.01) |
| *G06T 7/20* | (2006.01) |
| *G06K 9/00* | (2006.01) |

(52) U.S. Cl.
CPC ............... *G06T 2207/20056* (2013.01); *G06T 2207/30076* (2013.01); *G09G 2380/08* (2013.01)

(56) References Cited

U.S. PATENT DOCUMENTS

| | | | |
|---|---|---|---|
| 6,920,236 | B2 | 7/2005 | Prokoski |
| 6,958,809 | B2 | 10/2005 | Sterling et al. |
| 6,989,891 | B2 | 1/2006 | Braig et al. |
| 7,050,157 | B2 | 5/2006 | Braig et al. |
| 7,061,593 | B2 | 6/2006 | Braig et al. |
| 7,436,510 | B2 | 10/2008 | Grun et al. |
| 7,480,032 | B2 | 1/2009 | Braig et al. |
| 7,570,979 | B2 | 8/2009 | Cooper |
| 7,729,750 | B2 | 6/2010 | Tromberg et al. |
| 7,738,085 | B2 | 6/2010 | Braig et al. |
| 7,760,354 | B2 | 7/2010 | Grun et al. |
| 7,872,734 | B2 | 1/2011 | Braig et al. |
| 7,896,498 | B2 | 3/2011 | Munger et al. |
| 7,899,764 | B2 | 3/2011 | Martin et al. |
| 2002/0030154 | A1* | 3/2002 | Marchitto ............... A61B 5/113 250/221 |
| 2007/0100246 | A1* | 5/2007 | Hyde ................. A61B 5/02405 600/509 |
| 2009/0275808 | A1 | 11/2009 | DiMaio et al. |
| 2009/0318815 | A1 | 12/2009 | Barnes et al. |
| 2010/0249630 | A1 | 9/2010 | Droitcour et al. |
| 2010/0284082 | A1 | 11/2010 | Shpunt et al. |

OTHER PUBLICATIONS

Chen et al (Color structured light system of chest wall motion measurement for respiratory volume evaluation, 2010).*
Aoki et al (Extraction and visualization of cardiac beat by grid-based active stereo).*
Mestha et al., "3D Imaging Using Structured Light for Accurate Vehicle Occupancy Determination", U.S. Appl. No. 13/476,334, filed May 21, 2012.
Mestha et al., "Processing a Video for Vascular Pattern Detection and Cardiac Function Analysis", U.S. Appl. No. 13/483,992, filed May 30, 2012.
Xu et al., "Eliminating Artifacts From a Video of a Scene Illuminated With Unstructured and Structured Illumination Sources", U.S. Appl. No. 13/533,605, filed Jun. 26, 2012.
Wang et al., "Multi-Band Infrared Camera System Optimized for Skin Detection", U.S. Appl. No. 13/416,436, filed Mar. 9, 2012.
Xu et al., "Monitoring Respiration With a Thermal Imaging System", U.S. Appl. No. 13/103,406, filed May 9, 2011.
Cardoso et al., "Minimally Invasive Image-Based Determination of Carbon Dioxide (CO2) Concentration in Exhaled Breath", U.S. Appl. No. 13/246,560, filed Sep. 27, 2011.
Piratla et al., "Web-Based System and Method for Video Analysis", U.S. Appl. No. 13/417,979, filed Mar. 12, 2012.
Mestha et al., "Filtering Source Video Data Via Independent Component Selection", U.S. Appl. No. 13/281,975, filed Oct. 26, 2011.
Mestha et al., "Removing Environment Factors From Signals Generated From Video Images Captured for Biomedical Measurements", U.S. Appl. No. 13/401,207, filed Feb. 21, 2012.
Geng, Jason "Structured-Light 3D Surface Imaging: A Tutorial", by Jason Geng, Advances in Optics and Photonics vol. 3, pp. 128-160, Optical Society of America, Mar. 31, 2011.
Quan et al., "Shape measurement of small objects using LCD fringe projection with phase shifting," Optics Communications, vol. 189, pp. 21-29, 2001.
Groote et al., "Measurement of thoracoabdominal asynchrony: importance of sensor sensitivity to cross-section deformations," J. Appl. Physiol. 88, 1295-1302 (2000).
Levine et al., "Use of a triaxial magnetometer for respiratory measurements," J. Appl. Physiol. 70, 2311-2321(1991).
Allsop et al., "Application of long-period grating sensors to respiratory plethysmography," J. Biomed. Opt. 12, 064003 (2007).
Babchenko et al., "Fiber optic sensor for the measurement of respiratory chest circumference changes," J. Biomed. Opt. 4, 224-229 (1999).
Aliverti et al., "Optoelectronic plethysmography in intensive care patients," Am J Respir Crit Care Med 161, 1546-1552 (2000).
Saumarez, R.C., "Automated optical measurements of human torso surface movements during breathing," J. Appl. Physiol. 60, 702-709 (1986).
Ferrigno et al., "Three-dimensional optical analysis of chest wall motion," J. Appl. Physiol. 77, 1224-1231 (1994).
Aliverti et al., "Compartmental analysis of breathing in the supine and prone position by optoelectronic plethysmography," Ann. Biomed. Eng. 29, 60-70 (2004).
Chen et al., "Color structured light system of chest wall motion measurement for respiratory volume evaluation", J. Biomed. Opt. 15, 026013 (2010).
Drummond et al., "A video-based optical system for rapid measurements of chest wall movement," Physiol Meas 22, 489-503 (2001).
Zhang, Z., "A flexible new technique for camera calibration," IEEE Trans. on Pattern Analysis and Machine Intelligence, vol. 22(11), 1330-1334 (2000).
Poh et al., "Non-contact, automated cardiac pulse measurements using video imaging and blind source separation," Optics Express, vol. 18, No. 10, pp. 10762-10774, 2010.
Poh et al., "Advancements in non-contact, multiparameter physiological measurements using a webcam," IEEE Trans. on Biomedical Engineering, vol. 58, No. 1, Jan. 2011.
Rajapakse et al., "Approach and Applications of Constrained ICA," IEEE Trans. on Neural Networks, vol. 16, No. 1, Jan. 2005.
Moore, David, "A Real-World System for Human Motion Detection and Tracking", Final Thesis, California Institute of Technology, (2003).
Wang et al., "Intelligent Multimodal and Hyperspectral Sensing for Real-Time Moving Target Tracking", Applied Imagery Pattern Recognition Workshop (AIPR), pp. 1-8, (2008).
Al-Khalidi et al., "Tracking Human Face Features in Thermal Images for Respiration Monitoring", IEEE/ACS Int'l Conf. on Computer Systems and Applications (AICCSA), Hammamet, Tunisia, (May 16-19, 2010).
Fei et al., Analysis of Breathing Air Flow Patterns in Thermal Imaging, Proceedings of the 28th IEEE EMBS Annual International Conference, New York City, USA, pp. 946-952, (Aug. 30-Sep. 3, 2006).
Aoki et al., "Study on Respiration Monitoring Method Using Near-infrared Multiple Slit-lights Projection", IEEE International Symposium on Micro-NanoMechatronics and Human Science, pp. 291-296, (Nov. 7-9 2005), ISBN: 0-7803-9482-8.
Eveland et al., "Tracking Human Faces in Infrared Video", Image and Vision Computing, vol. 21, pp. 579-590 (2003).
Aoki et al., Non-contact and Unrestrained Respiration Monitoring System for Sleeping Person Using Near-infrared Bright Spots Matrix Irradiation, IEEJ Transactions on Electronics, pp. 1251-1258, vol. 124, No. 6, (Sep. 2004).
Murthy et al., Non-Contact Monitoring of Breathing Function Using Infrared Imaging, pp. 1-17, Technical Report No. UH-CS-05-09, Apr. 9, 2005.
Bernal et al., "Processing a Video for Tidal Chest Volume Estimation", U.S. Appl. No. 13/486,637, filed Jun. 1, 2012.
Bernal et al., "Minute Ventilation Estimation Based on Depth Maps", U.S. Appl. No. 13/486,682, filed Jun. 1, 2012.
Bernal et al., "Minute Ventilation Estimation Based on Chest Volume", U.S. Appl. No. 13/486,715, filed Jun. 1, 2012.
Tarvainen et al., "An Advanced De-Trending Method With Application to HRV Analysis", IEEE Trans. Biomed. Eng., vol. 49, No. 2, pp. 172-175, (Feb. 2002).

(56) References Cited

OTHER PUBLICATIONS

Philips Vital Signs Camera App, http://www.youtube.com/watch?v=2M7AFoqJyDI&feature=player, Feb. 8, 2012, two pages.

Jin et al., "Detection of respiratory rhythm from photoplethysmography signal using morphological operators", 3rd International Conference on Bioinformatics and Biomedical Engineering, 2009, pp. 1-4, ICBBE 2009.

* cited by examiner

PROCESSING A VIDEO FOR RESPIRATION RATE ESTIMATION

CROSS-REFERENCE TO RELATED APPLICATIONS

This patent application is a continuation in part of commonly owned and co-pending U.S. patent application Ser. No. 13/486,637 entitled: "Processing A Video For Tidal Chest Volume Estimation", by Bernal et al.

TECHNICAL FIELD

The present invention is directed to systems and methods for estimating a respiration rate by analyzing distortions in reflections of structured illumination patterns captured in a video containing at least a partial view of a thoracic region of a patient being monitored for respiratory function.

BACKGROUND

Monitoring respiratory events is of clinical importance in the early detection of potentially fatal conditions. Current technologies involve contact sensors the individual must wear constantly. Such a requirement can lead to patient discomfort, dependency, loss of dignity, and further may fail due to a variety of reasons including refusal to wear the monitoring device. Elderly patients and neo-natal infants are even more likely to suffer from the adverse effects of continued monitoring. Unobtrusive, non-contact, imaging based methods are increasingly desirable for respiratory function monitoring.

Prior methods capture video images of a region of interest of a subject and process the video to obtain physiological measurements relative to cardiac and respiratory function. These systems track a photoplethysmographic signal reflected off a region of exposed skin. The reflected signals are processed to identify and isolate components relating to a pulsating blood volume. If a region of exposed skin is absent then the video camera cannot register these signals. Although recordings of 2D videos of a non-skin region contain motion related information, previous attempts to isolate respiratory signals purely based on motion have not been successful. The present invention is directed to overcoming these drawbacks.

Accordingly, what is needed in this art are sophisticated systems and methods for estimating a respiration rate for a subject of interest captured in a video containing a view of that subject's thoracic region.

INCORPORATED REFERENCES

The following U.S. patents, U.S. patent applications, and Publications are incorporated herein in their entirety by reference.

"Processing A Video For Tidal Chest Volume Estimation", U.S. patent application Ser. No. 13/486,637, by Bernal et al.

"Minute Ventilation Estimation Based On Depth Maps", U.S. Pat. No. 8,971,985, by Bernal et al.

"Minute Ventilation Estimation Based On Chest Volume", U.S. patent application Ser. No. 13/486,715, by Bernal et al.

Processing A Video For Vascular Pattern Detection And Cardiac Function Analysis", U.S. Pat. No. 8,897,522, by Mestha et al.

"Multi-Band Infrared Camera System Optimized For Skin Detection", U.S. Pat. No. 9,171,196, by Wang et al.

Monitoring Respiration With A Thermal Imaging System", U.S. Pat. No. 8,790,269, by Xu et al.

"Filtering Source Video Data Via Independent Component Selection", U.S. Pat. No. 8,600,213, by Mestha et al.

"Removing Environment Factors From Signals Generated From Video Images Captured For Biomedical Measurements", U.S. Pat. No. 9,185,353, by Mestha et al.

"*An Advanced De-Trending Method With Application To HRV Analysis*", M. P. Tarvainen, P. O. Ranta-Aho, and P. A. Karjalainen, IEEE Trans. Biomed. Eng., Vol. 49, No. 2, pp. 172-175, (February 2002).

"*Structured-Light 3D Surface Imaging: A Tutorial*", by Jason Geng, Advances in Optics and Photonics Vol. 3, pp. 128-160, (Mar. 31, 2011) Optical Society of America.

"Respiratory Physiology: The Essentials", John B. West, Lippincott Williams & Wilkins; $9^{th}$ Ed. (2011), ISBN-13: 978-1609136406.

BRIEF SUMMARY

What is disclosed is a system and method for estimating a respiration rate for a subject of interest captured in a video containing a view of that subject's thoracic region. In one embodiment, a video of a target region of a body of a subject of interest is received. As more fully disclosed herein, motion of the subject's thoracic region is recorded in a video. Video image frames are processed to obtain a continuous time-series signal. This signal is then processed to obtain frequency information from which the subject's respiration rate can be isolated. Advantageously, measurements can be acquired under a diverse set of lighting conditions without disturbing the patient. The teachings hereof provide a non-contact approach to respiratory function monitoring that is particularly useful in intensive care units and at homes to aid in the detection of sudden deterioration of physiological conditions due to changes in respiration rate. The system and methods disclosed herein provide an effective tool for non-contact respiratory function analysis.

One embodiment of the present method for estimating respiration rate of a subject of interest being monitored for respiratory function in a non-contact, remote sensing environment involves performing the following. First, a video is received of a thoracic region of a subject of interest being monitored for respiratory function. The target region can be, for instance, the subject's anterior thoracic region, a region of the subject's dorsal body, or a side view containing the subject's thoracic region. The received video is captured using a video camera system and an illuminator configured to project a pattern of structured illumination onto the target region. The video camera is sensitive to electromagnetic radiation in a wavelength range that overlaps with the wavelength of the projected structured illumination. Each of the captured images of the video comprises data of sampled radiation emitted by a reflection of the illumination source off the subject's target region. The video image frames are processed to estimate 3D time-series data for the target region. In various embodiments, processing comprises, for each image of the video, comparing spatial attributes of the spatial distortion to known spatial attributes of undistorted projected patterns such that the distortion can be characterized in the image; calculating a depth map from the characterized distortion at different locations on the surface of the target region; and estimating a 3D volume from the depth map. After all the image frames of interest have been processed, the resulting sequence of estimated 3D volumes are concatenated to obtain the estimated 3D time-series data. The obtained 3D time-series data is de-trended to remove low frequency variations from the data. A FFT is performed on the de-trended data and automatic peak detection is used to extract the subject's respiration rate. In one embodiment, the subject's respiration rate is communicated to a display device for continuous monitoring of incremental changes in the respiration rate for the occurrence of PUHD Type I or PUHD Type II. Various embodiments are disclosed.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for estimating a respiration rate for a subject of interest by analyzing distortions in reflections of structured illumination patterns captured in a video containing a view of that subject's thoracic region.

Non-Limiting Definitions

Figure 1:
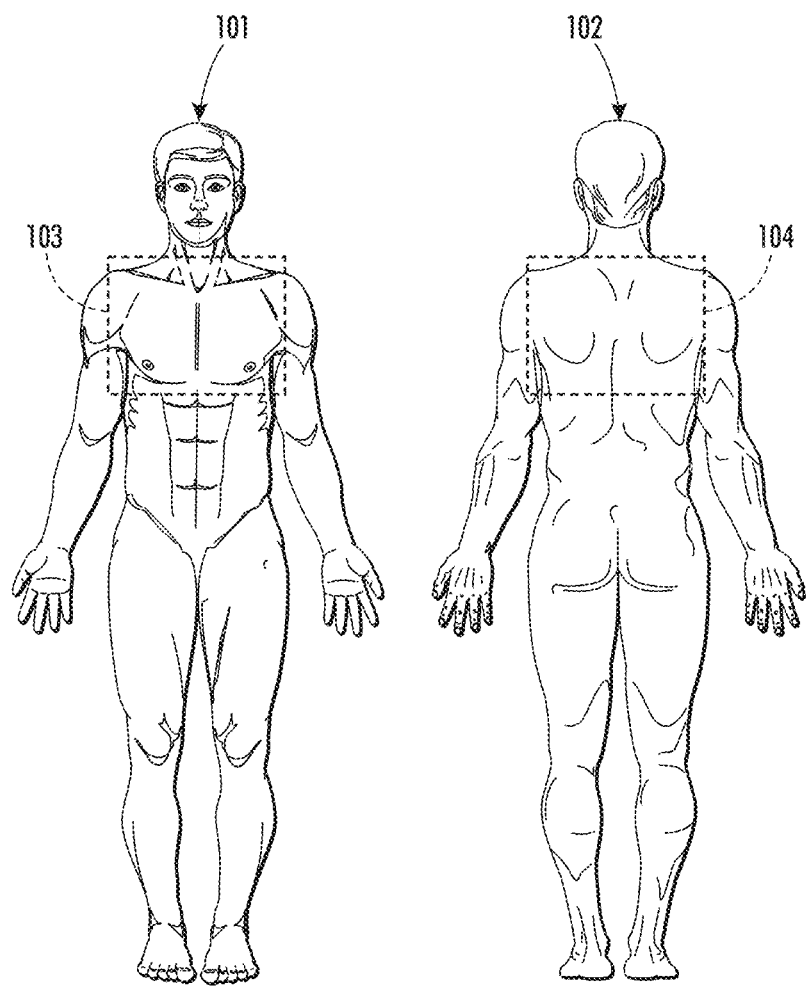
FIG. 1 shows both an anterior (frontal) view and a posterior (rear) view of an adult human.

A "subject of interest" refers to a subject being monitored for respiratory function such that a respiration rate can be determined for that subject in accordance with the teachings hereof. FIG. 1 shows an anterior (frontal) view 101 of an adult human as well as a posterior (rear) view 102. Target region 103 outlines the subject's anterior thoracic region. Target region 104 outlines the subject's posterior thoracic region. A target region, as used herein, also refers to any view of a region of the subject's body which performs a respiratory function. It should be appreciated that the use of the terms "human", "person", or "patient" herein is not to be viewed as limiting the scope of the appended claims solely to human subjects of interest. The teachings hereof apply equally to other subjects of interest which also have a respiratory function. Such additional subjects include, for example, mammals, birds, fish, and reptiles.

A "respiratory function" is a multi-stage process involving inhaling air into the lungs (inspiration), gas exchange, and exhaling air out of the lungs (expiration) followed by a post-expiratory pause. Inhalation causes the lungs contained within the chest cavity to fill with air thereby expanding chest volume. Inhalation is initiated by a diaphragm muscle and supported intercostal muscles. Under normal conditions, the diaphragm is the primary driver of inhalation. When the diaphragm contracts, the rib cage expands and the contents of the abdomen are moved downward. This results in a larger thoracic volume and negative pressure (with respect to atmospheric pressure) inside the thorax. Gas exchange is a primary function of the respiratory system. Molecules of gases are exchanged between the external environment and a blood circulation system in the pulmonary circuit. This exchange facilitates oxygenation of the blood and in turn tissues and removal of carbon dioxide and other metabolic wastes from the body. Gas exchange also helps maintain the acid-base balance of the body. The cellular mechanism of gas exchange is carried out by the simple phenomenon of pressure difference. When the atmospheric pressure is low outside, air from the lungs flow out into the environment. When the air pressure is low inside the lungs, the opposite occurs. Exhalation is generally a passive process due to the natural elasticity of lung tissue which causes them to recoil from the stretch of inhalation thus forcing air out until the pressures in the chest and the pressure of the outside atmosphere reach equilibrium. During forced exhalation, as when blowing out a candle, expiratory muscles including abdominal muscles and internal intercostal muscles, generate abdominal and thoracic pressure which helps to force air out of the lungs. During forced inhalation, as when taking a deep breath, external intercostal muscles and accessory muscles aid in expanding the thoracic cavity and bringing more air into the lungs. During vigorous inhalation (at rates exceeding 35 breaths per minute), or in an approaching respiratory failure, accessory muscles such as the sternocleidomastoid, platysma, the scalene muscles of the neck as well as the pectoral muscles and latissimus dorsi of respiration are recruited for support. A post-expiratory pause occurs when there is an equalization of pressure between the lungs and the atmosphere. The duration of the post-expiratory pause reduces with increased physical activity and may even fall to zero at high rates of exertion. When the subject is at rest, the duration of the post-expiratory pause is relatively long. The subject's respiration cycle is the time interval between the beginning of inhalation and the end of the post-expiratory pause. Immediately following the post-expiratory pause is the start of the next cycle.

Figure 2:
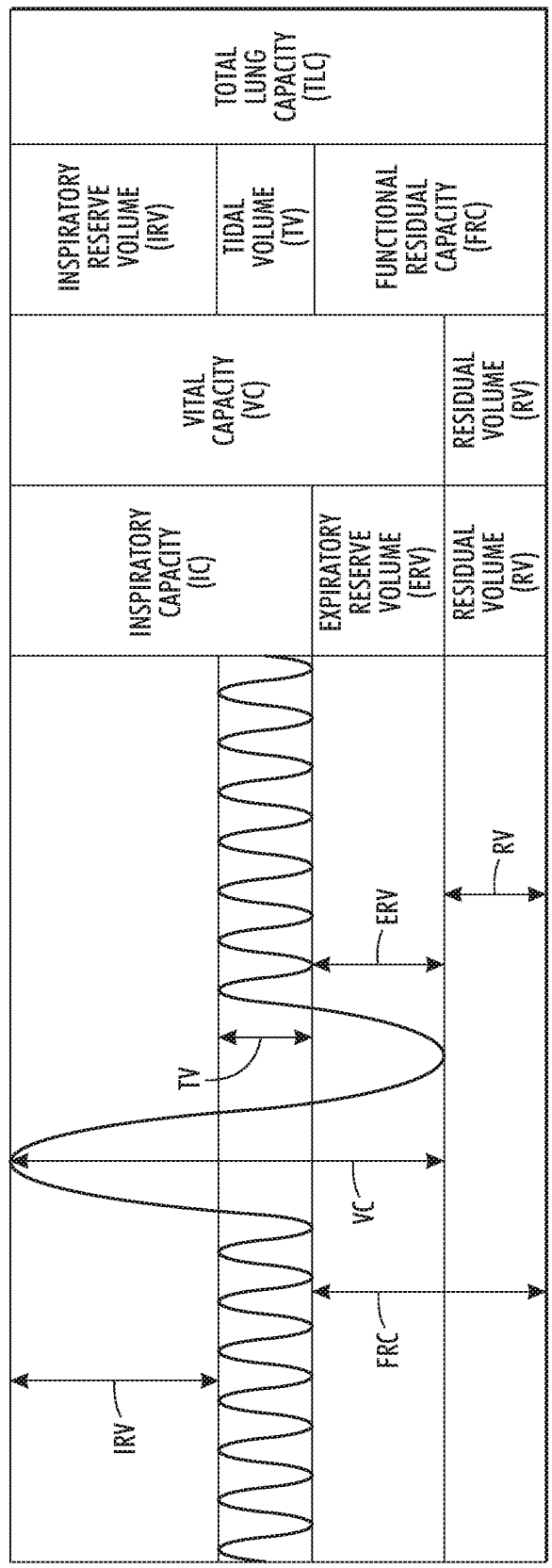
FIG. 2 plots the output of a spirometer of a normal person taking seven tidal breaths, followed by maximal inspiration and expiration.

"Respiration rate" refers to the number of breaths (inspiration and expiration) a subject takes within a certain amount of time (typically in breaths/minute). Respiration rate is often measured when a subject is at rest and simply involves determining the number of tidal breaths the subject takes per minute. A resting adult human takes between 12 and 20 tidal breaths per minute depending on the overall condition of that person's cardio-vascular and respiratory systems. Since total lung capacity of an average adult human is approximately 6.0 liters of air, the lungs displace a relatively small volume after inspiration and expiration while tidal breathing. Restrictive pulmonary diseases such as pulmonary fibrosis, pneumothorax, Infant Respiratory Distress Syndrome, and the like, decrease lung volume, whereas obstructive pulmonary diseases such asthma, bronchitis, and emphysema, obstruct airflow. FIG. 2 shows the output from a spirometer of a normal person taking seven tidal breaths, followed by maximal inspiration and expiration.

A "remote sensing environment" refers to a non-contact, unobtrusive non-invasive means of acquiring data from a subject, i.e., the sensing device does not physically contact the subject being sensed. The sensing device can be any distance away from the subject, for example, as close as less than an inch to as far as miles in the case of telemedicine. The teachings hereof find their intended uses in such a remote sensing environment such that the resting cardiac patient remains undisturbed.

A "video", as is generally understood, is a time-varying sequence of image frames captured over time using a video camera of a scene. A fully populated 2D image captured using, for example, a 3-channel color video camera is a 2D array of pixels with each pixel in the array having color values collected for pixels from each of those channels. A fully populated 2D image captured using, for example, a single channel video camera is a 2D array of pixels with each pixel in the array having an intensity value measured for that pixel location at a desired wavelength band of interest. The video may also contain other components such as, audio, time reference signals, and the like. The size of the video data may get large for longer video sequences. The video may also be processed or pre-processed to compensate for non-uniform illumination due to a curvature of a surface of the skin, for motion induced blur due to body or surface motion, imaging blur, and slow illuminant variation. Motion in the video may be compensated for using, for example, a video-based 2D image or 3D surface stabilization techniques.

"Receiving a video" is intended to be widely construed and means to retrieve, receive, capture with a video camera, or otherwise obtain a video for processing for tidal chest volume estimation in accordance with the present method. The video can be received from a memory or internal storage of the video camera system, or obtained from a remote device over a network. The video may also be retrieved from a media such as a CDROM or DVD. The video may be received by being downloaded from a website which makes such videos available for pre-processing or post-processing. One such web-based system is disclosed in the above-incorporated U.S. Pat. No. 8,712,126 entitled: "Web-Based System And Method For Video Analysis" by Piratla et al. The video can also be retrieved using an application such as those which are widely available for handheld cellular devices and processed on the user's cellphone or other handheld computing device such as an iPad.

A "video camera" refers to a device for capturing a video. The video camera can be a video camera that is sensitive in a visible wavelength range or an IR video camera that is sensitive in an infrared wavelength range such as the near infrared (NIR), short range infrared red (SWIR), mid-range infrared (MWIR), and long wave infrared (LWIR). The video camera may comprise a hybrid device that captures video in both the visible and infrared wavelengths.

A "structured illumination source" is a light source which projects source light through a patterned grid or window having known spatial characteristics. The pattern may be a pseudo-random pattern with known spatial characteristics. Accurate 3D surface profiles of objects in a scene can be computed using structured-light principles and triangulation-based image reconstruction techniques.

Example Video Capture System

Figure 3:
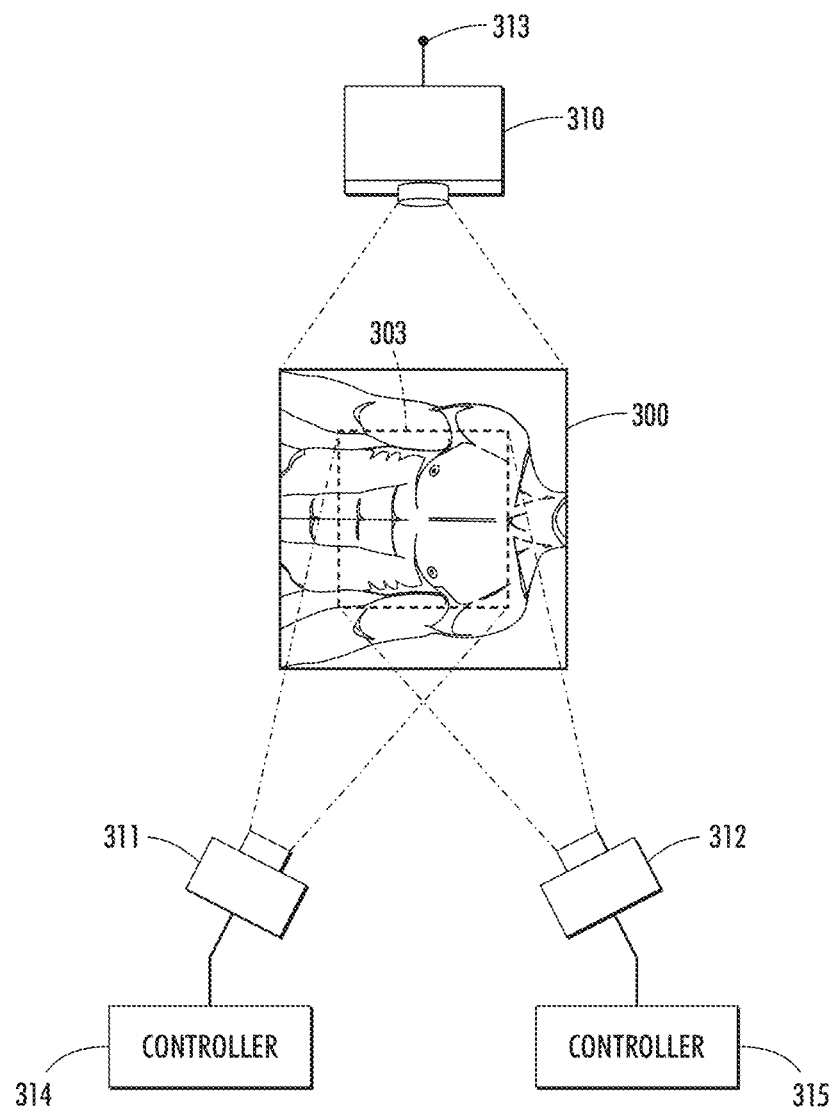
FIG. 3 illustrates an example scene illuminated with a structured light source and a video camera actively acquiring a video of a subject's chest area for respiration rate estimation in accordance with the teachings hereof.

Reference is now being made to FIG. 3 which shows a single 2D image frame 300 being captured of a target region 303 of the thoracic region of the subject of interest of FIG. 1. Video camera 310 captures reflected energy off the target region emitted by structured illumination source 311. Video camera 310 is shown having a communication element 313 to effectuate a bi-directional communication with a remote device, such as a computer workstation, wherein the video is received for processing. Controllers 314 and 315 are shown to effectuate a manipulation of structured illumination source 311 and 312, respectively, to reduce artifacts. Manipulation is required only to capture a video for extracting respiration rate, as opposed to other parameters. Methods for reducing such artifacts are disclosed in the above- incorporated reference: "Enabling Hybrid Video Capture Of A Scene Illuminated With Unstructured And Structured Illumination Sources", U.S. Pat. No. 9,155,475 by Xu et al. This reference discloses methods for reducing artifacts when there is switching between structured and unstructured illuminations. In the present application, a hybrid video capture may be utilized for capturing a first 2D image with structured illumination for estimating respiration rate followed by a second 2D image with unstructured illumination for heart rate estimation. It should be appreciated that such a system may be conceived when working in conjunction with systems that need unstructured illumination source for extracting other important physiological parameters. A video capture system may further comprise a video analysis module. In one embodiment, a video analysis module comprises a hardware device such as an ASIC with at least one processor capable of executing machine readable program instructions for analyzing video images on a frame-by-frame basis for respiration rate estimation in accordance with the teachings hereof. Such a module may also comprise, in whole or in part, a software application working alone or in conjunction with one or more hardware resources. Software applications may be executed by processors on different hardware platforms or emulated in a virtual environment. Aspects of the video analysis module may leverage off-the-shelf software.

Triangulation-Based 3D Image Reconstruction

Figure 4:
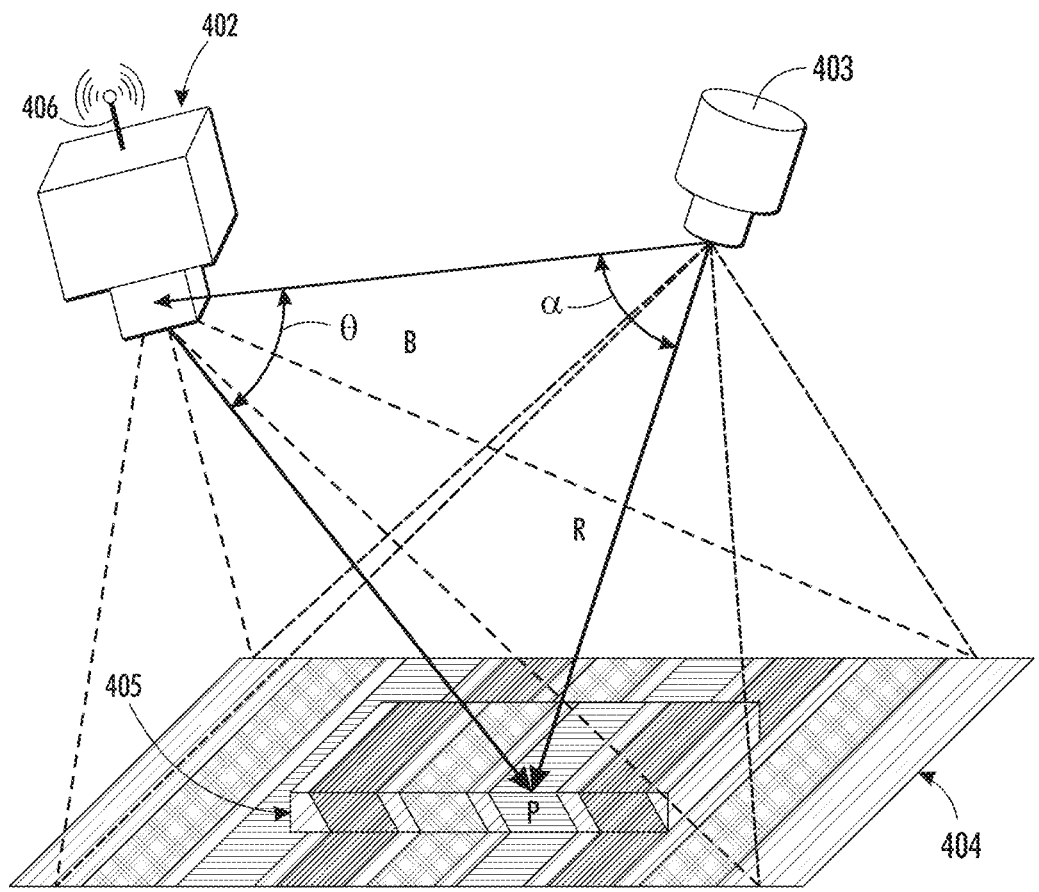
FIG. 4 shows the geometric relationships between an imaging sensor, a structured-light projector, and an object surface point expressed in terms of a triangulation.

A "depth map" is a map containing depth values based upon an analysis of the amount of distortion of a structured light pattern reflected from surfaces in that region of the image. Once the depth map has been generated, a volume can be calculated. In FIG. 4, structured illumination source 403 projects sinusoidal gratings 404 onto an object 405 and the reflection of the impinging sinusoidal gratings is captured by the camera system 402 as they reflect off the object. The sinusoidal gratings have known spatial characteristics of undistorted projected patterns. Camera system 402 is shown having a communication element 406 for bi-directional communication with a remote device, such as a workstation (not shown) wherein the captured video is communicated for processing. If the scene is a planar surface without any 3D surface variation and oriented approximately parallel to the camera sensor, the pattern shown in the acquired image will be similar to that of the projected structured-light pattern. However, when the surface is non-planar, is not parallel to the camera sensor or contains a 3D object 405, the shape of the object distorts the projected structured light pattern. Such light distortions can be detected by camera 402. The geometric relationship between camera 402, a structured illumination source 403, and point P on the surface of 3D object 405 can be expressed in terms of a triangulation as follows:

$$R = B \frac{\sin(\theta)}{\sin(\alpha + \theta)} \quad (1)$$

Figure 5:
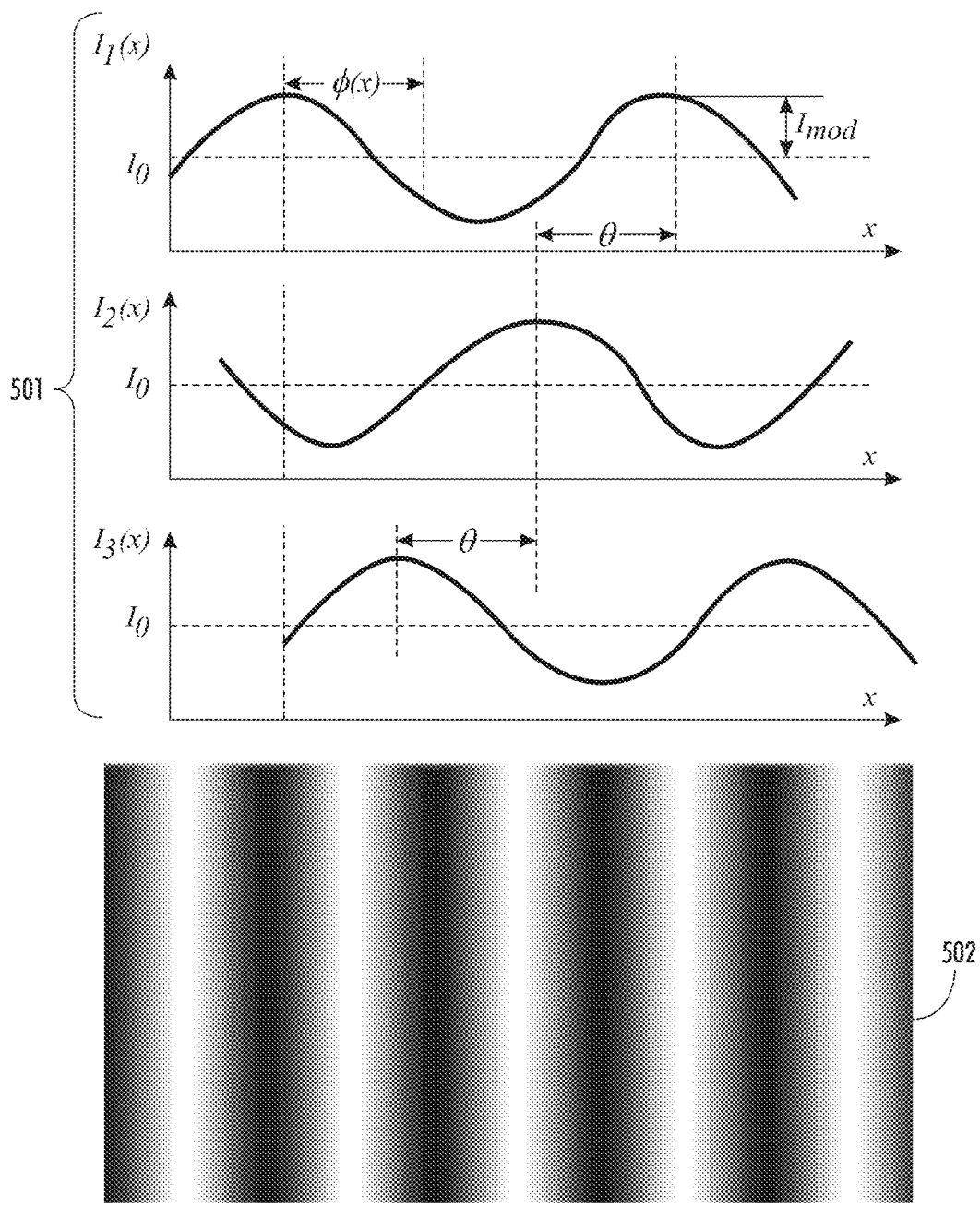
FIG. 5 shows the phase shift with three projection patterns and an example fringe image.

Accurate 3D image reconstruction can be based on a phase-shifting or phase modulation technique which measures phases at different locations on the object's surface and computes depth information from these phases. FIG. 5 shows the phase shift with three projection patterns, collectively at 501, projected onto the object surface, and an example fringe image 502. Image reconstruction via phase shift is a well-known method wherein intensities for each pixel (x,y) of the three projected fringe patterns are described by the following relationships:

$$I_1(x,y) = I_0(x,y) + I_{mod}(x,y)\cos(\phi(x,y)-\theta), \quad (2)$$

$$I_2(x,y) = I_0(x,y) + I_{mod}(x,y)\cos(\phi(x,y)), \quad (3)$$

$$I_3(x,y) = I_0(x,y) + I_{mod}(x,y)\cos(\phi(x,y)+\theta), \quad (4)$$

where $I_1(x,y)$, $I_2(x,y)$ and $I_3(x,y)$ are the intensities of three fringe patterns, $I_0(x,y)$ is the DC component (background), $I_{mod}(x,y)$ is the modulation signal amplitude, $\phi(x,y)$ is the phase, and $\theta$ is the constant phase-shift angle. Phase unwrapping is the process that converts the wrapped phase to an absolute phase. The phase information $\phi(x,y)$ can be retrieved (i.e., unwrapped) from the intensities in the three fringe patterns:

$$\phi' = \arctan\left[\sqrt{3}\,\frac{I_1(x,y) - I_3(x,y)}{2I_2(x,y) - I_1(x,y) - I_3(x,y)}\right] \quad (5)$$

Figure 6:
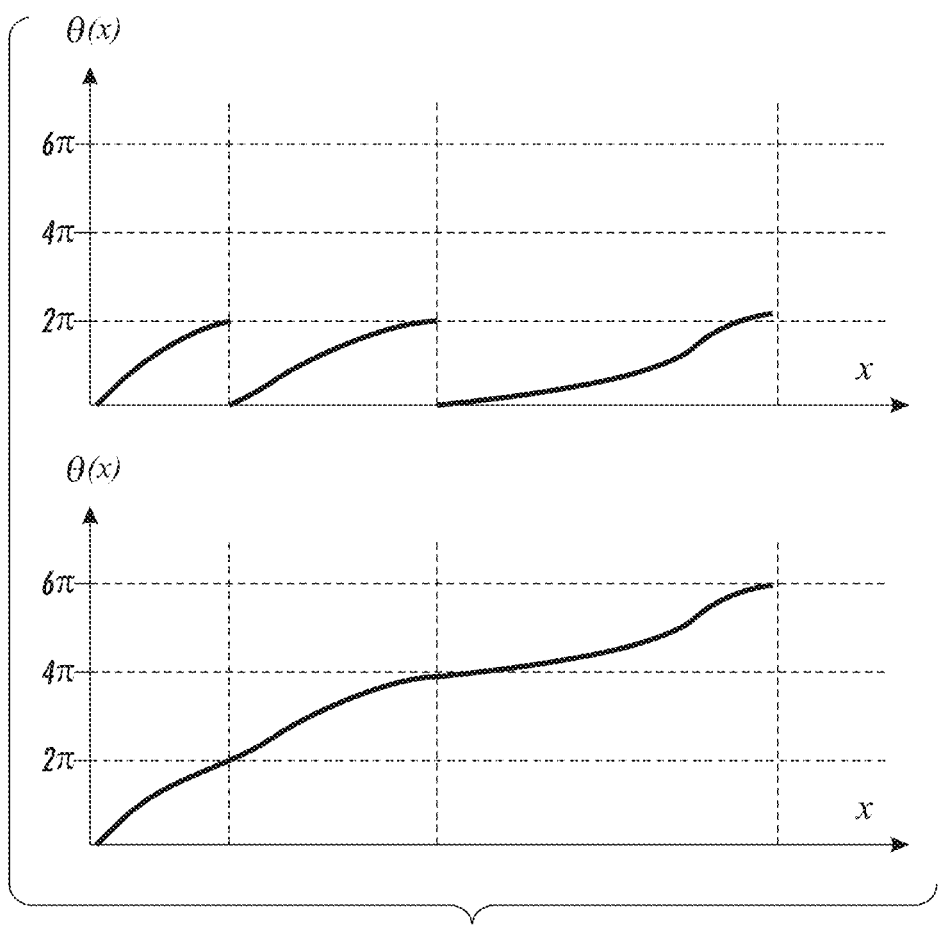
FIG. 6 illustrates one example embodiment of a phase unwrapping process.

The discontinuity of the arc tangent function at $2\pi$ can be removed by adding or subtracting multiples of $2\pi$ on the $\phi'(x,y)$ value (of FIG. 6):

$$\phi(x,y) = \phi'(x,y) + 2k\pi \quad (6)$$

where k is an integer representing projection period. Note that unwrapping methods only provide a relative unwrapping and do not solve for the absolute phase. The 3D (x,y,z) coordinates can be calculated based on the difference between measured phase $\phi(x,y)$ and the phase value from a reference plane.

Figure 7:
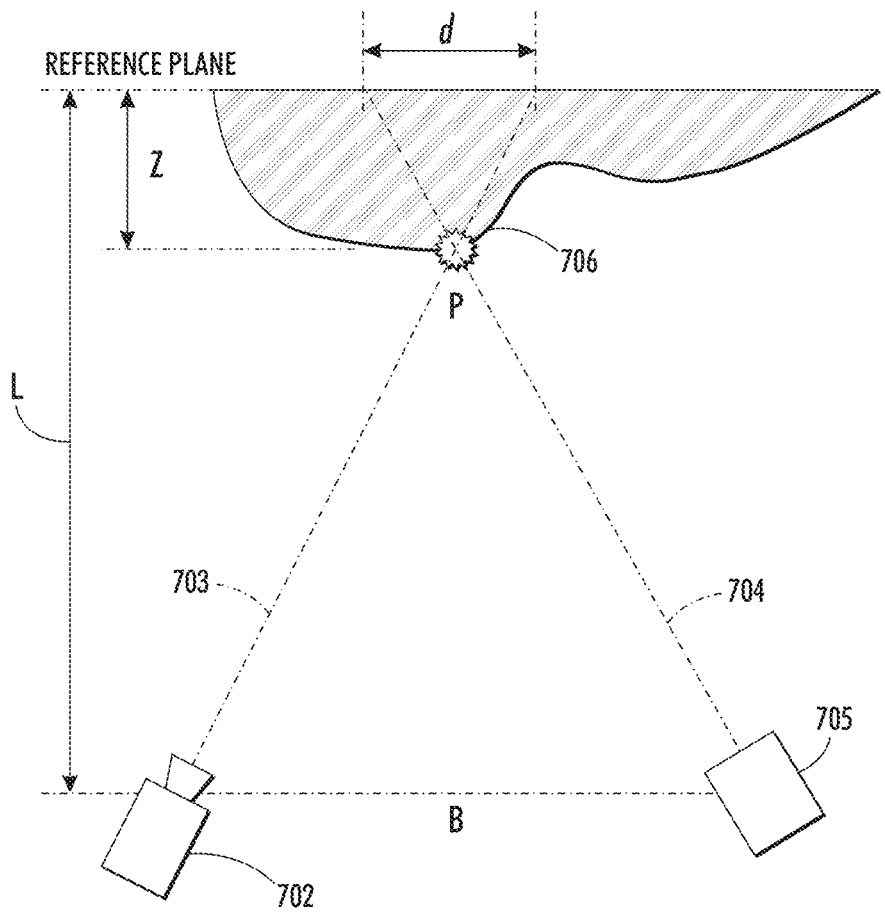
FIG. 7 shows a system which utilizes an image sensor to sense reflected light emitted by a patterned source projector in accordance with one embodiment hereof.

Reference is now being made to the system of FIG. 7 which utilizes a video camera 702 to sense reflected light emitted (at 704) projected by patterned illumination source projector 705 being reflected off point P of object 706, i.e., a location in the subject's thoracic region. Depth values are calculated by a geometry given by:

$$\frac{Z}{L-Z} = \frac{d}{B} \quad (7)$$

which reduces to:

$$Z \approx \frac{L}{B} d \quad (8)$$

Stripe indexing can also be used to achieve 3D surface reconstruction because the order in which the stripes are observed is not necessarily the same as the order in which the stripes are projected due to the inherent parallax existing in triangulation-based 3D surface imaging systems and the possibility to have stripes missing from the acquired image due to occlusion of 3D surface features. The collection of pixels forms the image. Use of color for stripe indexing in the projection patterns helps alleviate the ambiguity problem faced by phase-shift or multiple-stripe techniques using monochromatic patterns. This type of system enables encoding of multiple patterns into a single color projection image with each pattern possessing a unique color value. In order to reduce the decoding error rate, one can select a color set in which each color has a maximum distance from any other color in the set. The maximum number of colors is limited to a distance between colors that generates a minimal crosstalk in the acquired images. It should be appreciated that if the target 3D object is static, as in the case when the breathing stops for a short while, and the application does not impose stringent constraints on the acquisition time, multiple-shot (sequential) techniques can be used and may often result in more reliable and accurate results. On the other hand, if the target is moving, single-shot techniques are used to acquire a snapshot 3D surface image of the 3D object at a particular time instance. Single-shot techniques can be classified into techniques using continuously varying structured-light patterns, those using 1D encoding schemes (strip indexing), and those using 2D encoding schemes (grid indexing). Each technique has its own advantages and disadvantages, depending on the specific applications. Some techniques can be combined. For further information on 3D imaging techniques, the reader is respectfully directed to the above-incorporated reference entitled: "*Structured-Light 3D Surface Imaging: A Tutorial*", by Jason Geng.

It should also be appreciated that the illumination sources can be manipulated, i.e., spatially and/or spectrally varied during capture of the video by the video camera. An illumination source can be varied spatially by, for instance, moving that illumination source such that the source light is projected onto certain regions in the scene from different angles. An illumination source can be varied temporally by, for instance, toggling the projection of the source light on/off according to a schedule or a desired periodicity. An illumination source can be varied spectrally by, for instance, modifying the wavelength band of the electromagnetic radiation so that it doesn't interfere with other illumination sources and/or video cameras in the system. A device controller can be configured to vary the intensity of the source light that an illumination source projects.

Calibration

In order to convert the device-dependent depth readouts (in bytes) to device-independent well known metrics, a calibration needs to be performed. The calibration of the spatial coordinates of the device (from pixels to milliliters or meters or inches) can be performed in a manner which is substantially similar to the way a traditional RGB camera is calibrated. For example, the reference: "*A Flexible New Technique For Camera Calibration*", Z. Zhang, IEEE Trans. On Pattern Analysis and Machine Intelligence, Vol. 22(11), 1330-1334, (2000), teaches a method to estimate a spatial calibration model with unknown parameters. Calibration of the depth output requires knowledge of the geometric configuration of the stereo pair (illumination and imaging modules). Both the spatial coordinates and the depth readouts from the 3D imaging sensor can be translated into device independent units (such as milliliters or meters or inches). This, however, does not guarantee that the estimated volumes correspond to the volume being measured, given the fact that the changes in chest cage volume may not be identical to the changes in lung volume due to differences in elasticity between the two. Thus, additional calibration may be desirable. Assuming a linear relation between estimated and actual volume, a proportionality constant can be estimated via laboratory tests conducted for different breathing levels over a range required for the measurements. The actual volume can be measured using a spirometer. The slope of the linear regression line between the measurements of the spirometer and those obtained with the 3D imaging system would provide the calibration constant.

Segmentation

Before respiration rate can be estimated, the region of the depth map corresponding to the subject's body is preferably segmented in the images. This can be achieved in a plurality of ways. For example, since the distance from the camera to the bed's surface is known, the location of the subject's body can be extracted by detecting pixels surrounded by the bed's surface and located closer to the camera than the bed itself. Another method is to perform localization and then region-grow the target area to include pixels with similar depth information. This produces a resulting binary mask. Chest cage localization can be performed by judicious application of morphological operations on the binary mask that results from the body segmentation stage. For example, morphological opening of the mask with an appropriate size structuring element will remove pixels corresponding to the extremities and head given their relative size with respect to the chest area. Another way is to apply morphological skeletonization to the mask and determine the branch points of the resulting skeleton. These branch points will be approximately located at the neck and shoulders, thus providing indication of the location of the subject's thoracic region.

Estimating 3D Time-Series Data

Figure 8:
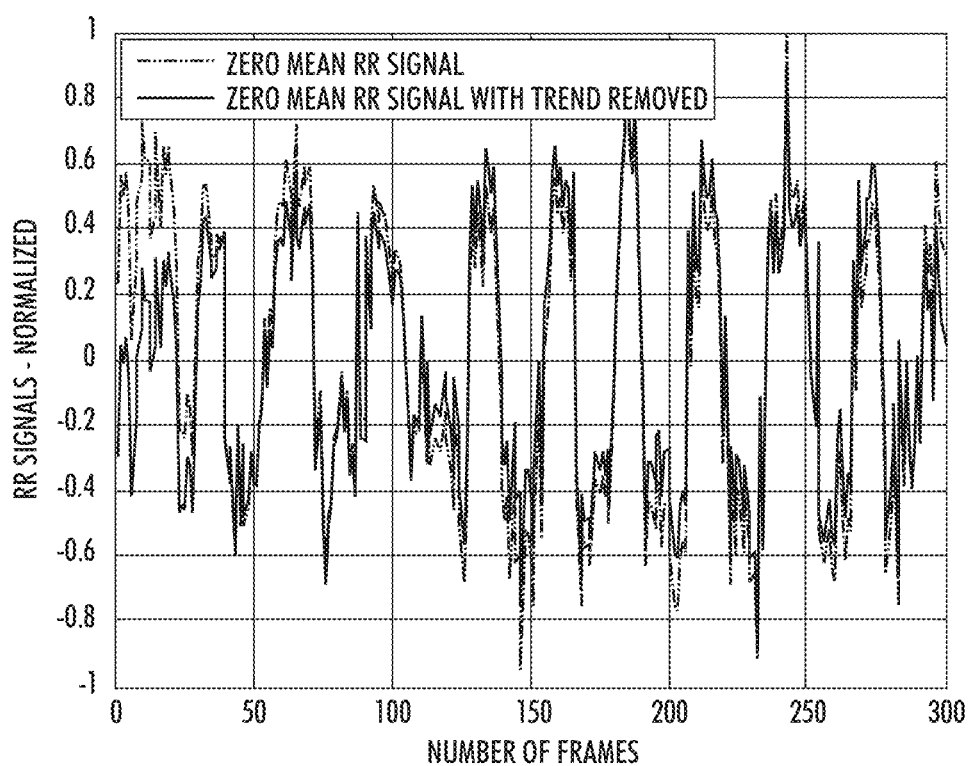
FIG. 8 shows a sample normalized zero-mean volumetric time-series signal for a 60 seconds period obtained from measurements from a male subject, and the de-trended time-series signal.

Time-series data is estimated by processing each image frame of the received video. Processing an image frame involves comparing spatial attributes of the captured spatial distortion to known spatial attributes of undistorted projected patterns such that the distortion can be characterized in the image. A depth map is then calculated from the characterized distortion at different locations on the surface of the target region. A 3D volume can be estimated for each image from the associated depth map. The resulting estimated 3D volumes obtained from the processed image frames are then concatenated together to produce the estimated 3D time-series data. In order to perform frequency analysis in the subsequent stages of the present method, normalization and mean subtraction are performed on the obtained time-series data. Normalization can be achieved by dividing the signal by its maximum value. FIG. 8 shows a sample normalized zero-mean volumetric time-series signal for a 60 seconds period obtained from measurements from a male subject.

De-Trending:

As the respiration rate is extracted from the normalized zero-mean time-series signal using a traditional FFT (i.e., spectral analysis) method, it is important for long-term continuous monitoring that the signal be stationary. A slow varying trend in the time-series signal can lead to a non-stationary signal component, which can then lead to large sub-bands around the respiration frequency. Also, in this particular case, de-trending can remove slow-varying, motion-induced frequency components. One method uses a smoothness approach as disclosed in the above-incorporated reference entitled: "*An Advanced De-Trending Method With Application To HRV Analysis*", M. P. Tarvainen, P. O. Ranta-Aho, and P. A. Karjalainen. This method operates like a time-varying high pass FIR filter by removing low frequency components. The de-trended, nearly stationary respiratory signal, $R_{stat}$, is obtained as follows:

$$R_{stat} = (I - (I + \lambda^2 D_2^T D_2)^{-1}) R_{original} \quad (10)$$

where, $R_{original}$ is the normalized zero removed time series signal, I is an identity matric, $\lambda$ is a parameter that is used to adjust the frequency response of the de-trending algorithm, T is the matrix transform operation, and $D_2$ is a second order difference matrix having a form:

$$D_2 = \begin{bmatrix} 1 & -2 & 1 & 0 & K & \ldots & \ldots & 0 \\ 0 & 1 & -2 & 1 & K & \ldots & \ldots & 0 \\ \ldots & \ldots & \ldots & \ldots & K & \ldots & \ldots & 0 \\ \ldots & \ldots & \ldots & \ldots & K & \ldots & \ldots & 0 \\ 0 & 0 & 0 & 0 & K & 1 & -2 & 1 \end{bmatrix} \quad (11)$$

If $R_{original}$ is of size N then I is an identify matrix of size N×N. The parameter $\lambda$ is set a priori by experimenting on a patient in their clinical/home/work environment with sample data in such a way that it does not lose any useful information from the lower frequency components.

Figure 9A:
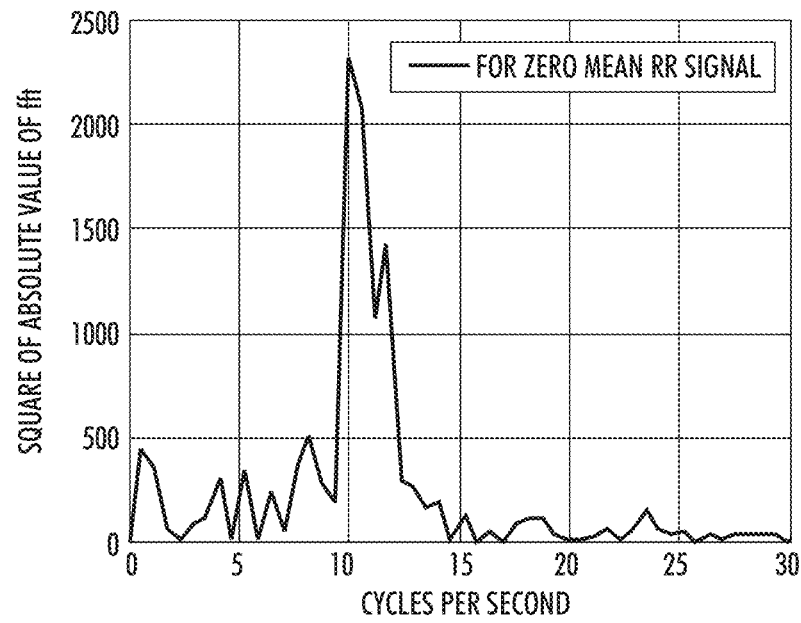
FIG. 9A shows the power spectral density curves for the respiration signals before de-trending.
Figure 9B:
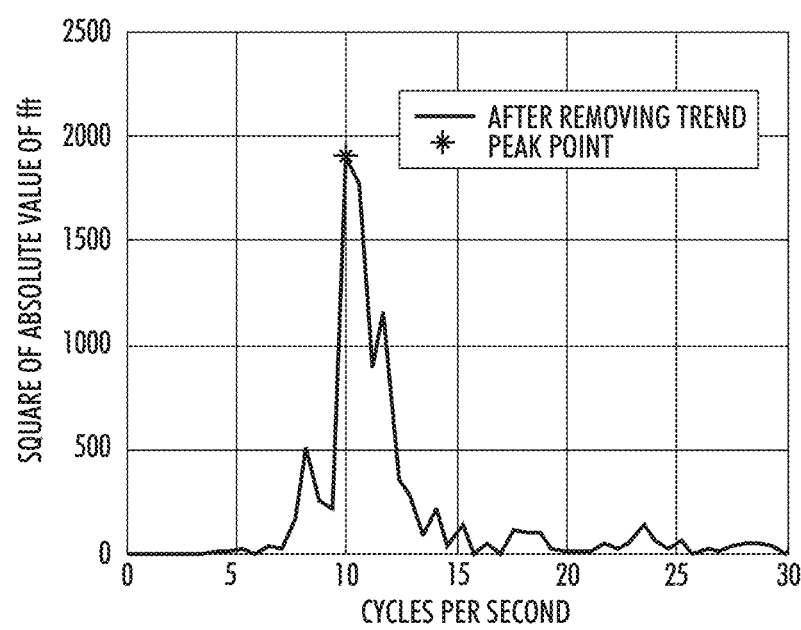
FIG. 9B shows the power spectral density curves for the respiration signals after de-trending ($\lambda=80$)

Spectral Analysis and Respiration Rate Detection:

Reference is now being made to FIGS. 9A-B which illustrate the use of a non-parametric approach (FFT based) for analyzing the spectra of the de-trended respiration time series signal. Non-parametric approaches such as the autoregressive (AR) time series modeling can also be used in place of the FFT. FIG. 9A shows the power spectral density curves for the respiration signals before de-trending. FIG. 9B shows the power spectral density curves for the respiration signals after de-trending ($\lambda$=80). Respiration rate was estimated by determining the location at which the spectral signature is maximum. On the basis of this analysis, a recording of 10 cycles per minute was observed in the one-minute interval which compares well with number of inspiration and expiration cycles in the original time series signal.

Flow Diagram of One Example Embodiment

Figure 10:
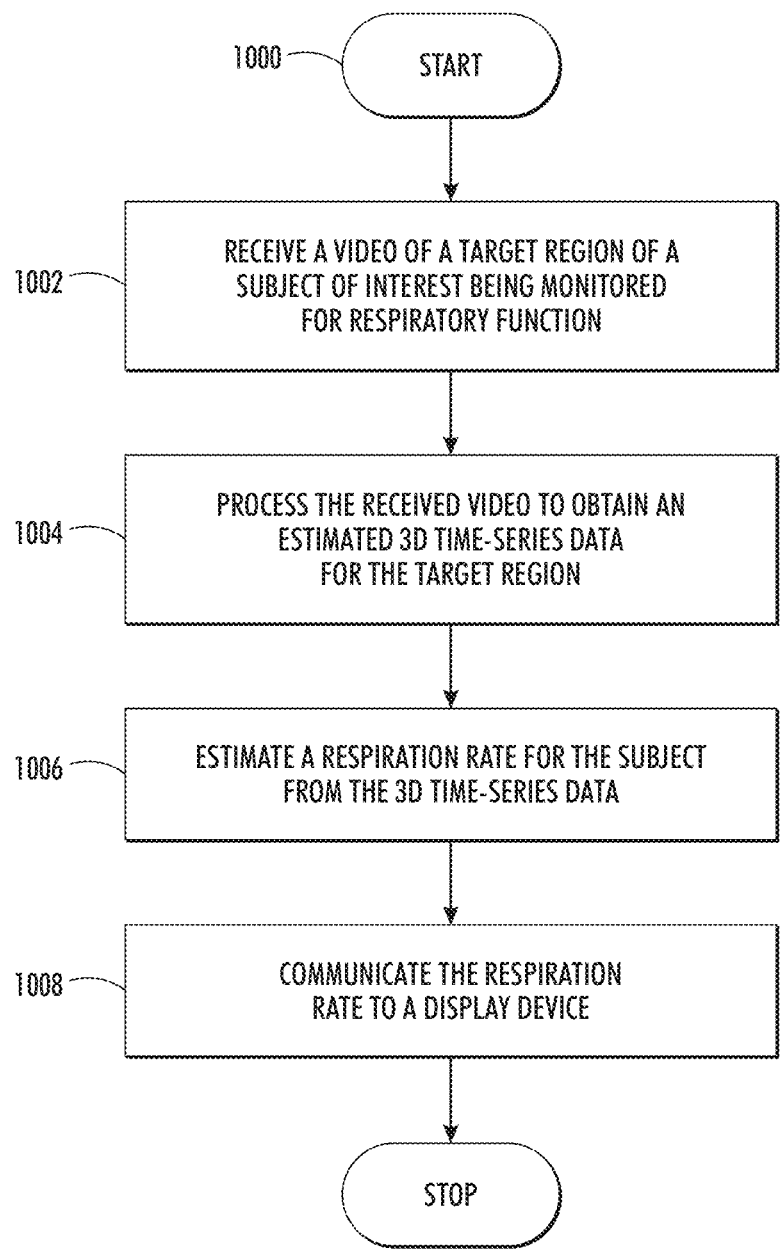
FIG. 10 is a flow diagram illustrating one example embodiment of the present method for respiration rate determination for a subject of interest being monitored for respiratory function.

Reference is now being made to the flow diagram of FIG. 10 which illustrates one example embodiment of the present method for respiration rate determination for a subject of interest being monitored for respiratory function. Flow processing begins at step 1000 and immediately proceeds to step 1002.

At step 1002, receive a video of a target region of a subject of interest being monitored for respiratory function. The video has been captured using a video camera and an illuminator configured to project a pattern of structured illumination. The video camera is configured to be sensitive to electromagnetic radiation in a wavelength of the structured illumination. Each image of the captured video comprises a sampling of radiation emitted by a reflection of the structured illumination off a surface of the target region. A spatial distortion is introduced by a reflection of the projected pattern off that surface. An example target region of a subject of interest is shown in FIG. 1.

At step 1004, process the video images to obtain estimated 3D time-series data for the target region.

At step 1006, estimate a respiration rate for the subject from the 3D time-series data.

At step 1008, communicate the respiration rate to a display device. In this embodiment, further processing stops. In another embodiment, an alarm is initiated which indicates that the subject's respiration rate is not within acceptable parameters. Initiating an alarm can be, for example, activating a light, making an audible noise, or otherwise generating a signal which activates a device which, in turn, performs an action or provides a notification. The kind of alarm signal being generated will depend on the particular embodiment wherein the teachings hereof are implemented. In this alternative embodiment, once the alarm signal is activated, further processing stops. In another embodiment, processing repeats such that the subject's respiration rate is continuously monitored. The present system can be used in conjunction with other health monitoring equipment or integrated therewith such that the initiated alarm signal causes these other device to perform intended functions.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Block Diagram of Video Processing System

Figure 11:
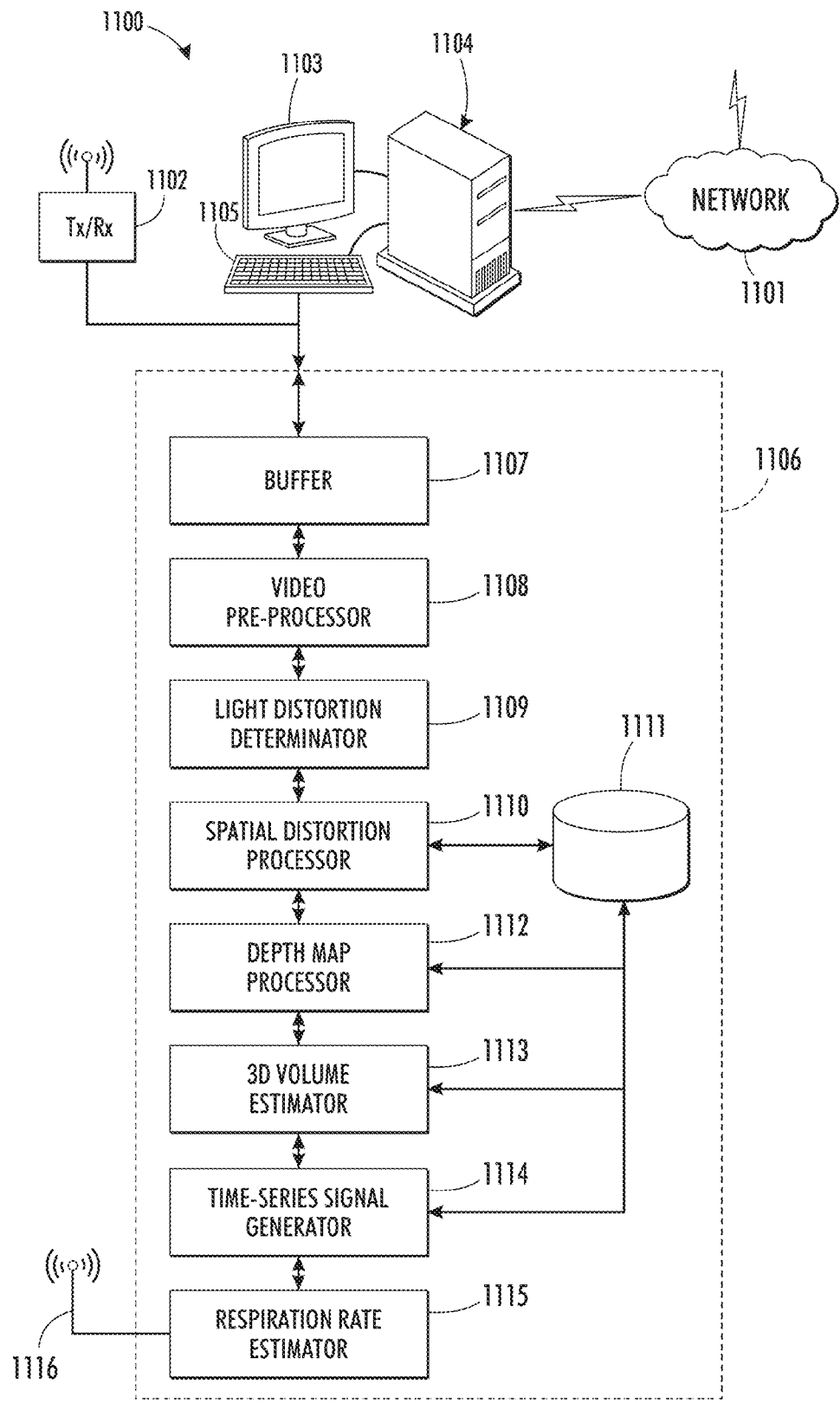
FIG. 11 illustrates a block diagram of one example video processing system for implementing various aspects of the present method as described with respect to the flow diagram of FIG. 10.

Reference is now being made to FIG. 11 which illustrates a block diagram of one example video processing system for implementing various aspects of the present method as described with respect to the flow diagram of FIG. 10.

In FIG. 10, a workstation 1100 is placed in communication with communication element 1102 for receiving detected structured illumination patterns from, for instance, video camera 310 of FIG. 3, and for otherwise effectuating communication between various devices and computer workstation 1100 via network 1101. Computer 1100 comprises display device 1103 for enabling a display of information and a keyboard 1105 for effectuating a user input or selection. An operator of the present system may use the graphical user interface of the workstation to identify or otherwise select images of the video for processing or re-processing, and provide a user input as may be required for the implementation hereof. The received video may be retrieved from a remote device over network 1101. Various portions of the video may be stored to a memory or storage device (not shown) in communication with workstation 1100 or may be communicated to a remote device over network 1101 via a communications such as device 1102 for remote storage or further processing. Workstation 1100 and communications device 1102 are in communication with Video Processing Unit 1106 for processing the video in accordance with the teachings hereof.

Video Processing Unit 1106 is shown comprising a buffer 1107. Such a buffer may be used for queuing information about the received image such as, for instance, one or more target regions within the image frames, size of the video, time/date information, and the like. The buffer may be configured to also store data, mathematical formulas and other representations to facilitate processing of the image in accordance with the teachings hereof. Video Pre-Processor 1108 performs any pre-processing of the video as may be desired or required to compensate for non-uniform illumination due to a curvature of a surface of the skin, for motion induced blur due to body or surface motion, imaging blur, and slow illuminant variation. Video Pre-Processor 1108 may be programmed to reduce the dimensionality of the data and perform Independent component analysis (ICA) on the video signal. Light Distortion Determinator 1009 determines an amount of distortion in the received reflected structured light pattern. Spatial Distortion Processor 1110 receives the determined amount of distortion and compares spatial attributes of the determined spatial distortions to known spatial attributes of undistorted projected patterns such that the distortion can be characterized in each image frame. The spatial distortions are provided to storage device 1111. Depth Map Processor 1112 retrieves the determined amount of spatial distortions from storage device 1111 and converts the distortion to a depth value, on a pixel-by-pixel basis for each frame of the video. A depth map is then generated from the characterized distortion at different locations on the surface of the target region and stored to storage device 1111. 3D Volume Estimator 1113 estimates a 3D volume from depth map, on a per frame basis. Time-Series Signal Generator 1114 retrieves the resulting estimated 3D volumes and concatenates these together to obtain the estimated 3D time-series data. Respiration Rate Estimator Module 1115 estimates the subject's respiration rate from the 3D time-series data, in a manner as disclosed herein. The subject's respiration rate is communicated to transmission element 1116 which, in turn, communicates the respiration rate to the patient's physician, for example, or to a nurse or respiratory therapist. Such a communication may include some or all of the original video and/or some or all of the obtained 3D time-series data. Some or all of the transmitted signals may, in turn, be communicated to workstation 1100 and displayed on a graphical display device 1103 for a visual review. In another embodiment, the patient's respiration rate is compared to one or more parameters which have been set for this patient, and a notification signal is initiated upon a determination that the subject's respiration rate is not within an acceptable limit or range. A notification signal may comprise an audible sound which provides an indication to a user or specialist that the subject requires attention. Such a notification may take the form of a canned audio message or, for instance, a bell tone sound or a sonic alert. The communicated notification message can be a text, audio, and/or video message, which may be communicated directly to a handheld cellular device. Such a notification may comprise, or additionally comprise, initiating a visible light which provides a visual notification such as, for instance, a blinking colored light. Such embodiments are intended to be encompassed within the scope of the appended claims.

The various modules and processing units of FIG. 11 are in communication with monitor 1103 to present thereon information for a user selection. Any of the modules and/or processing units of FIG. 11 are in communication with storage device 1111 via pathways shown and not shown and may store/retrieve data, parameter values, functions, pages, records, and machine readable/executable program instructions required to perform their various functions. Each of the modules and processing units of the Video Processing System 1106 is also in communication with workstation 1100 via pathways not shown and may further be in communication with one or more remote devices over network 1101. It should be appreciated that some or all of the functionality for any of the modules may be performed, in whole or in part, by components internal to the workstation. It should also be appreciated that the workstation has an operating system and other specialized software configured to display a variety of numeric values, text, scroll bars, pull-down menus with user selectable options, and the like, for entering, selecting, or modifying information displayed on display device 1103.

Various modules of the embodiments hereof may designate one or more components which may, in turn, comprise software and/or hardware designed to perform the intended function. A plurality of modules may collectively perform a single function. Each module may have a specialized processor capable of executing machine readable program instructions.

A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network.

One or more aspects of the methods described herein are intended to be incorporated in an article of manufacture, including one or more computer program products, having computer usable or machine readable media. For purposes hereof, a computer usable or machine readable media is, for example, a floppy disk, a hard-drive, memory, CD-ROM, DVD, tape, cassette, or other digital or analog media, or the like, which is capable of having embodied thereon a computer readable program, one or more logical instructions, or other machine executable codes or commands that implement and facilitate the function, capability, and methodologies described herein. Furthermore, the article of manufacture may be included on at least one storage device readable by a machine architecture or image processing system embodying executable program instructions capable of performing the methodology described in the flow diagrams.

Various presently unforeseen or unanticipated alternatives, modifications, variations, or improvements therein may become apparent and/or subsequently made by those skilled in the art, which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for estimating respiration rate of a subject of interest being monitored for respiratory function in a non-contact, remote sensing environment, the method comprising:
    receiving a video of a target region of a body of a subject of interest being monitored for respiratory function, wherein said video is captured using a video camera and an illuminator configured to project a pattern of structured illumination, said video camera being sensitive to electromagnetic radiation in a wavelength of said structured illumination, each image of said captured video comprising a sampling of radiation emitted by a reflection of said structured illumination off a surface of said target region, a spatial distortion being introduced by a reflection of said projected pattern off said surface;
    processing said video images to reconstruct 3D depth information of the scene and estimate 3D time-series data from said 3D depth information for said target region; and
    estimating said subject's respiration rate from said 3D time-series data comprising:
    for each image of said video:
        comparing spatial attributes of said spatial distortion to known spatial attributes of undistorted projected patterns such that said distortion can be characterized in said image;
        calculating a depth map from said characterized distortion at different locations on said surface of said target region;
        estimating a 3D volume from said depth map; and
        concatenating said resulting estimated 3D volumes to obtain said estimated 3D time-series data.

2. The method of claim 1, wherein said video camera comprises one of: a video camera that is sensitive in a visible wavelength range, and an IR video camera that is sensitive in an infrared wavelength range.

3. The method of claim 2, wherein said infrared wavelength range comprises any of: near infrared (NIR), short range infrared red (SWIR), mid-range infrared (MWIR), and long wave infrared (LWIR).

4. The method of claim 1, wherein said target region comprises one of: said subject's anterior thoracic region, a region of said subject's dorsal body, and a side view containing said subject's thoracic region.

5. The method of claim 4, further comprising:
    de-trending said obtained 3D time-series data to remove low frequency variations from said data;
    performing a Fast Fourier Transform on said de-trended time-series data; and
    performing automatic peak detection to extract said respiration rate.

6. The method of claim 1, further comprising monitoring incremental changes in said respiration rate for an occurrence of any of: PUHD Type I and PUHD Type II.

7. The method of claim 1, wherein said video is captured using multiple video cameras with non-zero disparity among them with respect to the scene to form stereo vision of the scene, said video cameras being sensitive to the same electromagnetic radiation in a wavelength of interest.

8. The method of claim 1, further comprising monitoring said respiration signal for detecting sudden infant death.

9. The method of claim 1, further comprising monitoring said respiration signal for detecting respiratory function in sleep apnea patients.

10. A system for estimating respiration rate of a subject of interest being monitored for respiratory function in a non-contact, remote sensing environment, the system comprising:
    an illuminator configured to project a pattern of structured illumination;
    a video camera for capturing a video of a target region of a subject of interest being monitored for respiratory function, said video camera being sensitive to at least the electromagnetic radiation in a wavelength of said structured illumination, wherein said video is captured using a video camera and an illuminator configured to project a pattern of structured illumination, said video camera being sensitive to electromagnetic radiation in a wavelength of said structured illumination; and
    a processor in communication with said video camera and a display device, said processor executing machine readable program instructions for performing:
        receiving video captured by said video camera, each image of said video comprising a sampling of radiation emitted by a reflection of said structured illumination off a surface of said target region, a spatial distortion being introduced by a reflection of said projected pattern off said surface;

processing said video to estimate 3D time-series data for said target region;

estimating a respiration rate from said 3D time-series data comprising:

for each image of said video:

comparing spatial attributes of said spatial distortion to known spatial attributes of undistorted projected patterns such that said distortion can be characterized in said image;

calculating a depth map from said characterized distortion at different locations on said surface of said target region;

estimating a 3D volume from said depth map; and concatenating said resulting estimated 3D volumes to obtain said estimated 3D time-series data; and communicating said estimated respiration rate to said display device.

11. The system of claim 10, wherein said video camera comprises one of: a video camera that is sensitive in a visible wavelength range, and an IR video camera that is sensitive in an infrared wavelength range.

12. The system of claim 11, wherein said infrared wavelength range comprises any of: near infrared (NIR), short range infrared red (SWIR), mid-range infrared (MWIR), and long wave infrared (LWIR).

13. The system of claim 10, wherein said target region comprises one of: said subject's anterior thoracic region, a region of said subject's dorsal body, and a side view containing said subject's thoracic region.

14. The system of claim 13, further comprising:

de-trending said obtained 3D time-series data to remove low frequency variations from said data;

performing a Fast Fourier Transform on said de-trended time-series data; and performing automatic peak detection to extract said respiration rate.

15. The system of claim 10, further comprising monitoring incremental changes in said respiration rate for an occurrence of any of: PUHD Type I and PUHD Type II.

16. The system of claim 10, wherein said video is captured using multiple video cameras with non-zero disparity among them with respect to the scene to form stereo vision of the scene, said video cameras being sensitive to the same electromagnetic radiation in a wavelength of interest.

17. The system of claim 10, further comprising monitoring said respiration signal for detecting sudden infant death.

18. The system of claim 10, further comprising monitoring said respiration signal for detecting respiratory function in sleep apnea patients.

19. A computer implemented method for estimating respiration rate of a subject of interest being monitored for respiratory function in a non-contact, remote sensing environment, the method comprising:

receiving a video of a target region of a body of a subject of interest being monitored for respiratory function, said video being captured using a video camera and an illuminator configured to project a pattern of structured illumination, said video camera being sensitive to electromagnetic radiation in a wavelength of said structured illumination, each image of said captured video comprising a sampling of radiation emitted by a reflection of said structured illumination off a surface of said target region, a spatial distortion being introduced by a reflection of said projected pattern off said surface;

processing said video images to estimate 3D time-series data for said target region;

estimating said subject's respiration rate from said 3D time-series data comprising:

for each image of said video:

comparing spatial attributes of said spatial distortion to known spatial attributes of undistorted projected patterns such that said distortion can be characterized in said image;

calculating a depth map from said characterized distortion at different locations on said surface of said target region;

estimating a 3D volume from said depth map; and concatenating said resulting estimated 3D volumes to obtain said estimated 3D time-series data; and communicating any of: said respiration rate and said 3D time-series data, to a display device for visual review.

20. The computer implemented method of claim 19, further comprising:

de-trending said obtained 3D time-series data to remove low frequency variations from said data;

performing a Fast Fourier Transform on said de-trended time-series data; and performing automatic peak detection to extract said respiration rate.

* * * * *